US008079106B2

(12) United States Patent
Yang

(10) Patent No.: US 8,079,106 B2
(45) Date of Patent: Dec. 20, 2011

(54) ELECTRICAL TOOTH BRUSH

(76) Inventor: Alex Tzutsan Yang, Las Vegas, NV (US)

( * ) Notice: Subject to any disclaimer, the term of this patent is extended or adjusted under 35 U.S.C. 154(b) by 960 days.

(21) Appl. No.: 11/109,226

(22) Filed: Apr. 18, 2005

(65) Prior Publication Data

US 2006/0230555 A1 Oct. 19, 2006

(51) Int. Cl.
*A61C 17/26* (2006.01)

(52) U.S. Cl. ........................................ 15/23; 15/22.1

(58) Field of Classification Search ............ 15/23, 22.1, 15/248.1
See application file for complete search history.

(56) References Cited

U.S. PATENT DOCUMENTS

| | | | | |
|---|---|---|---|---|
| 1,854,626 A * | 4/1932 | Riggall, Jr. | ........................ | 15/23 |
| 3,739,416 A * | 6/1973 | Kurachi | ........................ | 15/23 |
| 4,275,749 A * | 6/1981 | Caroli | ........................ | 15/23 |
| 4,335,480 A * | 6/1982 | Liu | ........................ | 15/23 |

* cited by examiner

*Primary Examiner* — Laura C Guidotti

(74) *Attorney, Agent, or Firm* — Raymond Y. Chan; David and Raymond Patent Firm

(57) ABSTRACT

An electrical toothbrush includes an elongated handle body, a motor received in the handle body to drive a driving shaft to rotate, and a brush head including an elongated brush arm detachably mounted to the driving shaft and arranged when the driving shaft is driven to rotate, the brush arm is rotated correspondingly and a plurality of brushing bristles radially and outwardly extended from the brush arm for generating a rolling motion to substantially brush a user's teeth when the brush arm is driven to rotate, wherein the brush arm is arranged for locating at a position that the brushing bristles are tangentially rolling on the tooth surface to brush the tooth surface and are consequently brush the gumline at a predetermined angle to remove plaque from the areas between teeth and around the gums.

3 Claims, 4 Drawing Sheets

32
312
31
311
20
22
332
33
331
12
21
25
24
11
23
10
13

ELECTRICAL TOOTH BRUSH

BACKGROUND OF THE PRESENT INVENTION

1. Field of Invention

The present invention relates to a dental instrument, and more particularly to an electrical toothbrush, which can effectively clean the teeth and gums by inspiring a proper brushing motion.

2. Description of Related Arts

Gum disease (periodontitis) is one of the common dental problems. Periodontal disease, especially in the early stages, is usually not painful such that many people having gum disease do not even realize it. Researches report that the periodontal disease is an infection in the gums caused by the bacteria in plaque, wherein plaque and bacteria build up on and between the teeth, especially at the sidewall of the tooth and along the gumline. To prevent the gum disease, dentists always suggest having a better oral hygiene by brushing and flossing regularly. By reducing the amount of plaque on your teeth, you can reduce the amount of bacteria in your mouth.

Brushing method is the most common method for removing plaque built-up on the teeth. Accordingly, the proper brushing for effectively cleaning teeth and gums is that the bristles of the toothbrush should place along the gumline at a 45 degree angle such that the bristles 3A can contact both the tooth surface 1A and the gumline 2A. Then, the bristles 3A should be gently brushed the tooth surface 1A two to three times using a vibrating back and forth rolling motion, as shown in FIG. 1. It is worth to mention that the bristles 3A of the toothbrush should maintain a 45 degree angle with the gumline 2A to remove the plaque from the areas between teeth and around the gums.

Accordingly, the arrangement of the bristles is important since the bristles directly contact the teeth and the gumline. A conventional toothbrush comprises a brush head that the bristles are alignedly formed on the brush head in row. By using the conventional toothbrush, the user may merely take 10 minutes to complete the brushing with the above mentioned brushing method. However, studies show that each person will spend 2 to 5 minutes to complete the brushing. In other words, the improper brushing habit influences plaque accumulation.

An electric toothbrush is introduced to reduce the brushing time because the brush head is powered to provide a high-frequent brushing motion of the bristles. One common type of electrical toothbrushes provides a circular brushing motion for the bristles such that the bristles can substantially brush on the teeth surface. However, the circular brushing motion of the bristles cannot remove the plaque from the areas between teeth and around the gums in accordance with the proper brushing of placing the bristles along the gumline at a 45 degree angle and gently brushing the tooth surface with rolling motion. In other words, the circular brushing motion of the bristles can only “polish” the teeth surface.

Another common type of the electrical toothbrush provides an ultrasonic for the bristles to break the plaque from the areas between teeth and around the gums by means of vibration. However, in order to effectively clean the teeth and gum, a brushing force must be applied on the bristles to actually brush on the teeth surface to remove the plaque along the gumline. In addition, such ultrasonic-electrical toothbrush violates the rule of proper brushing.

As a result, due to the structural configuration of the electrical toothbrush, the bristles of the toothbrush cannot effectively remove the plaque from the areas between teeth and around the gums, especially the areas inaccessible to the toothbrush. Thus, an improper brushing the gumline may even cause the gum bleeding.

SUMMARY OF THE PRESENT INVENTION

A main object of the present invention is to provide an electrical toothbrush which can effectively clean the teeth and gums by inspiring a proper brushing motion.

Another object of the present invention is to provide an electrical toothbrush, wherein a brush head is driven to rotate such that bristles radially projected from the brush head generates a rolling motion to brush the teeth along the gumline at a 45 degree angle.

Another object of the present invention is to provide an electrical toothbrush, wherein the brushing operation is easy and simple by placing the brush head at the gumline, the bristles brush the gumline at a 45 degree angle to effectively remove the plaque therewithin.

Another object of the present invention is to provide an electric toothbrush, which provides a high-frequent rolling motion of the bristle to effectively brush the teeth and to plaque, so as to reduce the brushing time in comparison with the conventional toothbrush.

Another object of the present invention is to provide an electrical toothbrush, wherein the brush head is adapted to rotate in both clockwise and counter clockwise directions to substantially contact with the teeth surface and gumline.

Accordingly, in order to accomplish the above objects, the present invention provides an electrical toothbrush, comprising:

an elongated handle body having a receiving cavity and a coupling end;

a power unit comprising a motor received in the receiving cavity and a driving shaft which is outwardly extended from the coupling end of the handle body and is driven to rotate by the motor; and a brush head, which comprises:

an elongated brush arm detachably mounted to the driving shaft and arranged when the driving shaft is driven to rotate, the brush arm is rotated correspondingly; and a plurality of brushing bristles radially and outwardly extended from the brush arm for generating a rolling motion to substantially brush a user’s teeth when the brush arm is driven to rotate, wherein the brush arm is arranged for locating at a position that the brushing bristles are tangentially rolling on the tooth surface to brush the tooth surface and are consequently brush the gumline at a predetermined angle to remove plaque from the areas between teeth and around the gums.

These and other objectives, features, and advantages of the present invention will become apparent from the following detailed description, the accompanying drawings, and the appended claims.

DETAILED DESCRIPTION OF THE PREFERRED EMBODIMENT

Figure 2:
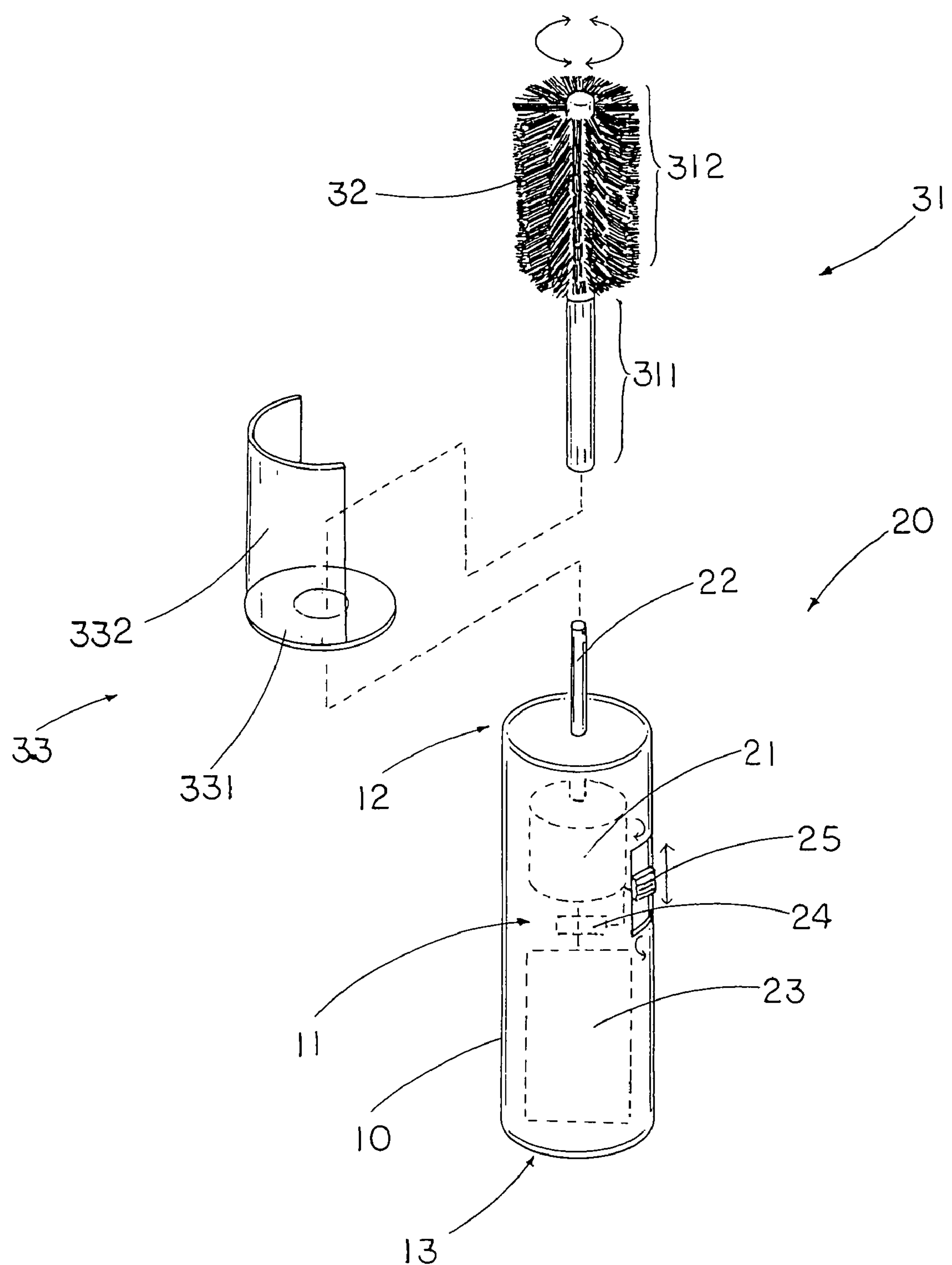
FIG. 2 is an exploded perspective view of an electrical toothbrush according to a preferred embodiment of the present invention.

Referring to FIG. 2 of the drawings, an electric toothbrush according to a preferred embodiment of the present invention is illustrated, wherein the electrical toothbrush comprises an elongated handle body 10 having a receiving cavity 11 and a coupling end 12, and a power unit 20 comprising a motor 21 received in the receiving cavity 11 and a driving shaft 22 which is outwardly extended from the coupling end 12 of the handle body 10 and is driven to rotate by the motor 21.

The electrical toothbrush further comprises a brush head 30 which comprises an elongated brush arm 31 detachably mounted to the driving shaft 22 and arranged when the driving shaft 22 is driven to rotate, the brush arm 31 is rotated correspondingly, and a plurality of brushing bristles 32 radially and outwardly extended from the brush arm 31 for generating a rolling motion to substantially brush a user's teeth 1 when the brush arm 31 is driven to rotate. In which, the brush arm 31 is arranged for locating at a position that the brushing bristles 32 are tangentially rolling on the tooth surface 2 to brush the tooth surface 2 and are consequently brush the gumline 3 at a predetermined angle to remove plaque from the areas between teeth 1 and around the gums. In addition, the rolling motion of the brushing bristles 32 is adapted to scrub the biting surface of the teeth and brush against the tongue to remove odor-producing bacteria.

According to the preferred embodiment, the handle body 10 is shaped and sized adapted for the user to hold the handle body 10 to locate the brushing bristles 32 within the mouth of the user. In addition, the power unit 20 is received in the receiving cavity 11 of the handle body 10 in a water-sealed manner for preventing water entering into the receiving cavity 11 during the brushing operation.

Figure 1:
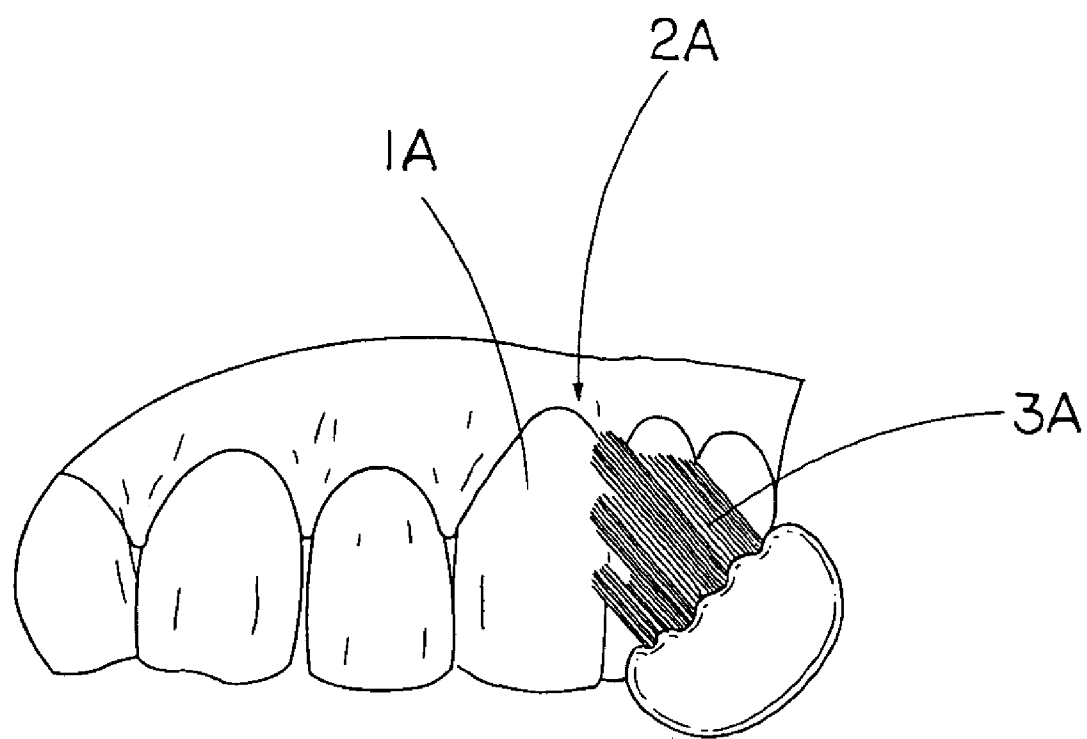
FIG. 1 is a side view of a conventional toothbrush, illustrating the bristles of the conventional toothbrush maintaining a 45 degree angle with the gumline.

As shown in FIG. 1, the power unit 20 further comprises a rechargeable battery 23 received in the receiving cavity 11 of the handle body 10 to electrically connect with the motor 21. The handle body 10 further has a recharging end 13 electrically extended from the rechargeable battery 23 for recharging the rechargeable battery 23 when the recharging end 13 of the handle body 10 is electrically connected to a power source. Alternatively, a replaceable battery can be used as a substitution of the rechargeable battery 23 to replacably receive in the receiving cavity 11 for electrically connecting with the motor 21.

Accordingly, the driving shaft 22 is outwardly protruded from the coupling end 12 of the handle body 10 in a rotatably movable manner to detachably couple with the brush head 30 at the coupling end 12 of the handle body 10, as shown in FIG. 2.

The brush arm 31 has an inserting end portion 311 for the driving shaft 22 slidably inserting thereinto and a bristle end portion 312 that the brushing bristles 32 are radially and outwardly projected from the bristle end portion 312 of the brush arm 31. Accordingly, only the bristle end portion 312 of the brush arm 31 is driven to rotate to roll the brushing bristles 32 through the driving shaft 22 when the brush arm 31 is coupled at the coupling end 12 of the handle body 10 to affix the inserting end portion 311 of the brush arm 31 in a non-rotational manner. In other words, the driving shaft 22 is extended through the inserting end portion 311 of the brush arm 31 to couple with the bristle end portion 312 of the brush arm 31. It is worth to mention that, as an alternative, the driving shaft 22 is coupled with the inserting end portion 311 of the brush arm 31 wherein the inserting end portion 311 of the brush arm 31 can be integrally extended from the bristle end portion 312 thereof such that when the driving shaft 22 is driven to rotate, the entire brush arm 31, i.e. including the inserting end portion 311 and the bristle end portion 312, is rotated to roll the brushing bristles 32.

Figure 3:
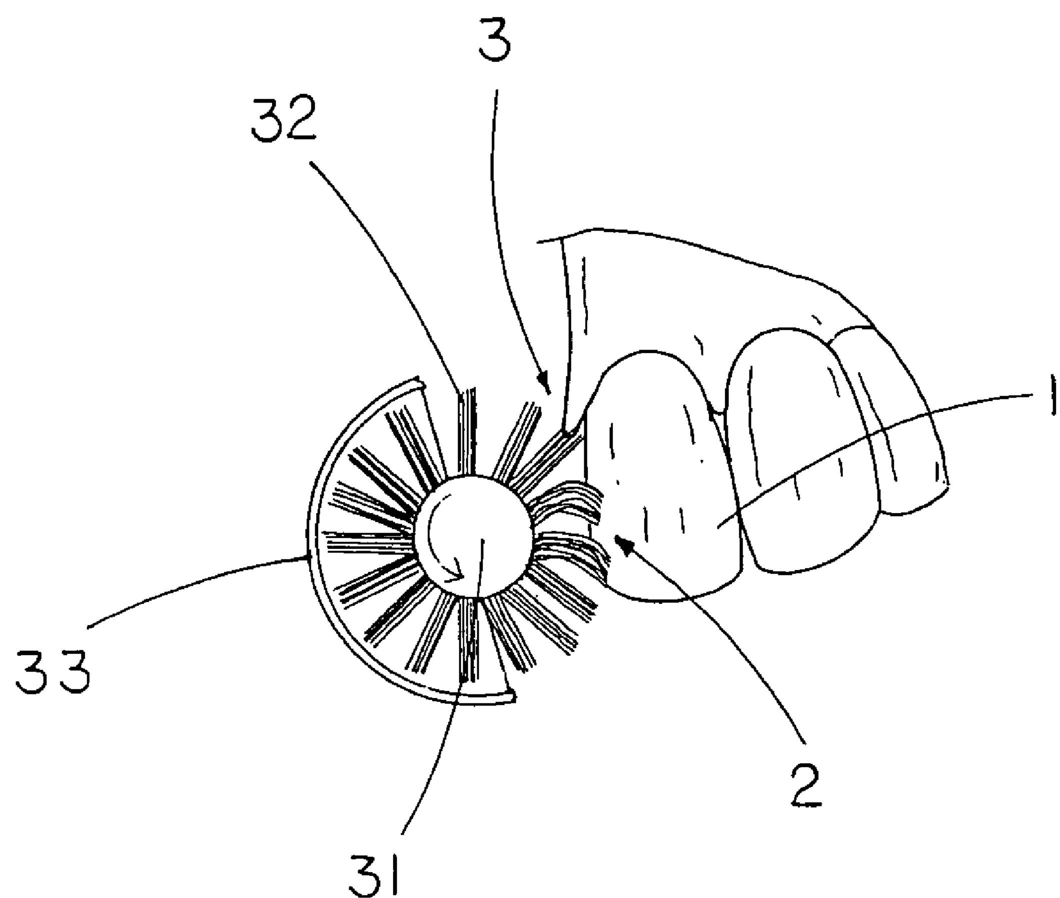
FIG. 3 is a schematic view of a brush head of the electrical toothbrush according to the above preferred embodiment of the present invention, illustrating the brushing bristles providing a rolling motion to brush the teeth along the gumline.

The brushing bristles 32 are made of nylon and/or polyester that adapted for removing plaque without damaging to the gums. The brushing bristles 32 are alignedly formed along the bristle end portion 312 of the brush arm 31 in a row manner wherein the rows of the brushing bristles 32 are radially extended from the brush arm 31 such that when the brush arm 31 is driven to rotate, the free end portions of the brushing bristles 32 are tangentially rolling on the tooth surface 2 to brush the tooth surface 2. Since the brushing bristles 32 are radially projected from the brush arm 31, the brushing bristles 32 brush the gumline 3 at a predetermined angle, approximately 45 degrees, to remove plaque from the areas between teeth 1 and around the gums. It is worth to mention that the rolling motion of the brushing bristles 32 brushes the tooth surface 2 and the gumline 3 consequently so as to efficiently brush the teeth 1 while being time effective, as shown in FIG. 3.

Accordingly, the bristle end portion 312 of the brush arm 31 has a predetermined length that the brushing bristles 32 are projected therealong for brushing against the tooth surface 2. In addition, the brushing bristles 32 are adapted to fit into a gap between each two teeth 1 so as to substantially clean the side surface of each of the teeth 1.

According to the preferred embodiment, the power unit 20 further comprises a control circuit 24 disposed in the receiving cavity 11 to electrically connect the motor 21 and a control switch 25 which is provided on the handle body 10 and is arranged to activate the control circuit 24 to control a rotational direction of the brush arm 32 via the driving shaft 22. Therefore, the brush arm 32 is adapted to be driven to rotate at either the clockwise direction or the counter clockwise direction. Therefore, the user is able to easily actuate the brush arm 32 at one rotational direction to brush the upper set of the teeth 1 while turn the brush arm 32 at the opposed rotational direction to brush the lower set of the teeth 1. It is worth to mention that when brushing the teeth 1, the brush arm 31 is set to rotate the brushing bristles 32 to brush the teeth 1 at the rotational direction from the tooth surface 2 to the gumline 3, as shown in FIG. 3.

Furthermore, the control circuit 24 is arranged to control the rotational speed of the brush arm 31 via the driving shaft 22 by switching the control switch 25 such that the user is able to selectively adjust the rotational speed of the brush arm 31 to control the rolling motion of the brushing bristles 32. Therefore, the user is able to control the control circuit 24 and the position of the brush arm 32 with respect to the teeth 1 to brush the gumline so as to prevent the gum bleeding and receding gumline. Timer control and low battery indicator can also be set in the control circuit 24 to set the operation time of the motor 21 and to indicate the electrical power condition of the rechargeable battery 23 respectively.

Figure 4:
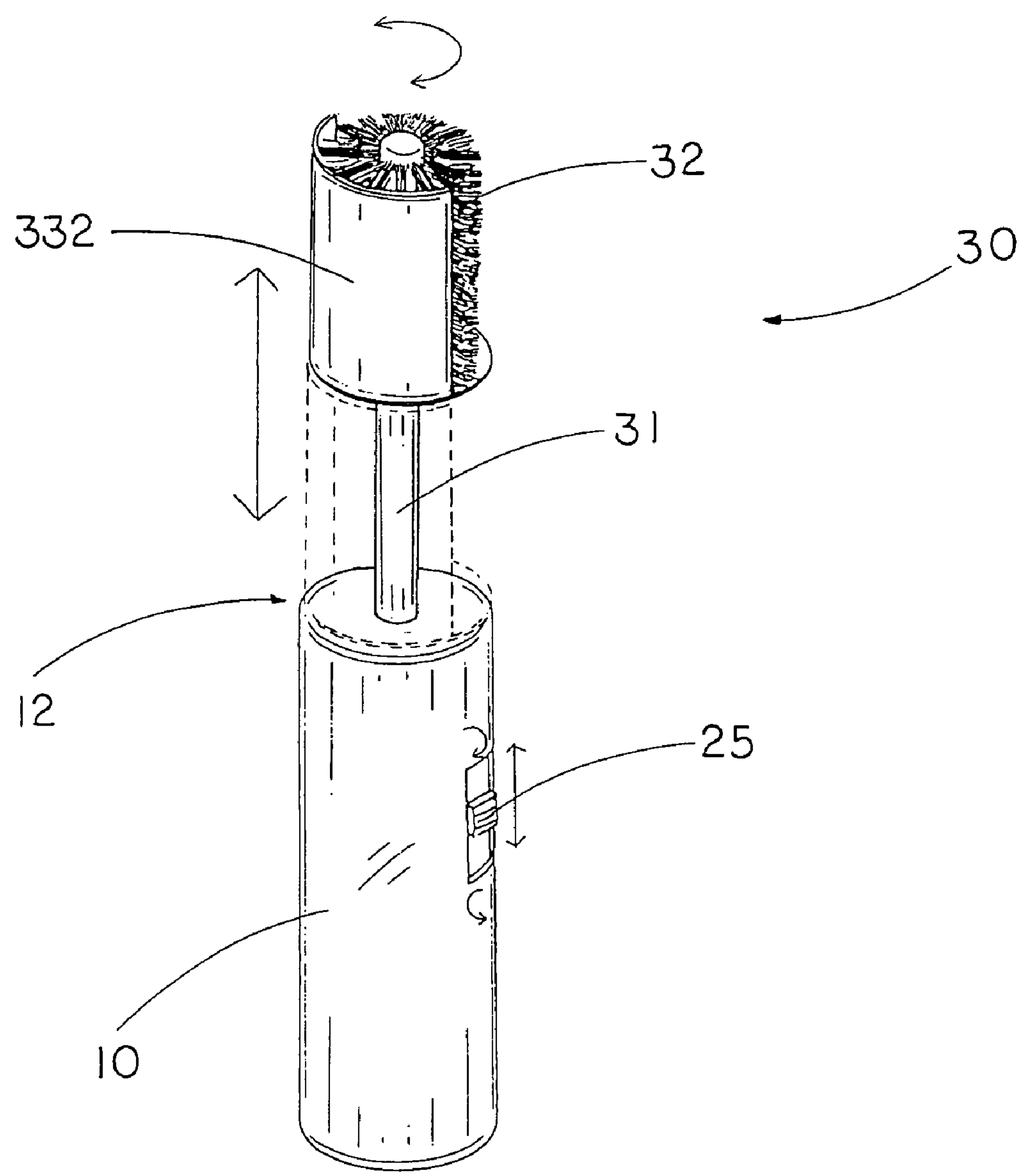
FIG. 4 is a perspective view of the electrical tooth brushing according to the above preferred embodiment of the present invention, illustrating the sliding movement of the spitting shelter.

As shown in FIG. 4, the brush head 30 further comprises a spitting shelter 33 slidably mounted to the brush arm 31 to partially cover the brushing bristles 32 for preventing water spitting therefrom during the brushing operation. Accordingly, the spitting shelter 33 comprises a sliding joint 331 slidably mounted at the inserting end portion 311 of the brush arm 31 and a bristle shelter 332 having a C-shaped cross section upwardly extended from the sliding joint 331 and arranged when the sliding joint 331 is upwardly slid towards the bristle end portion 312 of the brush arm 31, the bristle shelter 332 covers the brushing bristles 32 which are not brushing on the tooth surface 2. It is worth to mention that when the brushing bristles 32 brush the incisor teeth, the spitting shelter 33 is adapted to block the water spitting at the brushing bristles 32 out of the mouth. When the brushing bristles 32 brush the molar teeth, the spitting shelter 33 prevents the brushing bristles 32 directly contacting with the oral cavity so as to prevent the oral tissues from being damaged.

Accordingly, the sliding joint 331 has a slider through hole having a size slightly larger than a size of the inserting end portion 311 of the brush arm 31 wherein the brush arm 31 is slidably passing through the slider through hole of the sliding joint 331 to slidably mount the spitting shelter 33 to the brush arm 31. Thus, the length of the bristle shelter 332 is substantially longer than the bristle end portion 312 of the brush arm 31 to cover the brushing bristles 32.

One skilled in the art will understand that the embodiment of the present invention as shown in the drawings and described above is exemplary only and not intended to be limiting.

It will thus be seen that the objects of the present invention have been fully and effectively accomplished. It embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A brush head for detachably mounting to an electrical toothbrush having a driving shaft to generate a rotational power, comprising:

an elongated brush arm adapted for detachably mounting to said driving shaft and arranged when said driving shaft is driven to rotate, said brush arm is rotated correspondingly;

a plurality of brushing bristles radially and outwardly extended from said brush arm for generating a rolling motion to substantially brush a user's teeth when said brush arm is driven to rotate, wherein said brush arm is arranged for locating at a position that said brushing bristles are tangentially rolling on the tooth surface to brush the tooth surface and are consequently brush the gumline at a predetermined angle to remove plaque from the areas between the teeth and around the gums, wherein said brush arm has an inserting end portion for said driving shaft slidably inserting thereinto and a bristle end portion that said brushing bristles are radially and outwardly projected from said bristle end portion of said brush arm in a row manner; and a spitting shelter slidably mounted to said brush arm to partially cover said brushing bristles for blocking water spitting at said brushing bristles, wherein when said brushing bristles brush user's teeth, said spitting shelter is arranged to prevent said brushing bristles from directly contacting with an oral cavity of said user so as to prevent oral tissues of said user from being damaged, wherein said spitting shelter comprises a sliding joint slidably mounted at said brush arm and a C-shaped bristle shelter upwardly extended from said sliding joint, wherein when said sliding joint is slid upwardly along said inserting end portion of said brush arm, said bristle shelter covers said brushing bristles which are not brushing on the tooth surface, wherein said sliding joint has a slider through hole having a size slightly larger than a size of said inserting end portion of said brush arm, wherein said inserting end portion of said brush arm is slidably passing through said slider through hole of said sliding joint to slidably mount said spitting shelter to said brush arm, wherein said bristle end portion of said brush arm is adapted for coupling with said driving shaft through said inserting end portion of said brush, such that only said bristle end portion of said brush arm is driven to rotate said brushing bristles.

2. An electrical toothbrush, comprising:

an elongated handle body having a receiving cavity and a coupling end;

a power unit comprising a motor received in said receiving cavity, a driving shaft which is outwardly extended from said coupling end of said handle body and is driven to rotate by said motor, and a control circuit disposed in said receiving cavity to electrically connect said motor, and a control switch provided on said handle body; and a brush head, which comprises:

an elongated brush arm detachably mounted to said driving shaft and arranged when said driving shaft is driven to rotate, said brush arm is rotated correspondingly, wherein said control circuit is activated by said control switch to control a rotational direction of said brush arm; and a plurality of brushing bristles radially and outwardly extended from said brush arm for generating a rolling motion to substantially brush a user's teeth when said brush arm is driven to rotate, wherein said brush arm is arranged for locating at a position that said brushing bristles are tangentially rolling on the tooth surface to brush the tooth surface and are consequently brush the gumline at a predetermined angle to remove plaque from the areas between the teeth and around the gums, wherein said brush arm has an inserting end portion for said driving shaft slidably inserting thereinto and a bristle end portion that said brushing bristles are radially and outwardly projected from said bristle end portion of said brush arm in a row manner;

wherein said brush head further comprises a spitting shelter slidably mounted to said brush arm to partially cover said brushing bristles for blocking water spitting at said brushing bristles, wherein when said brushing bristles brush user's teeth, said spitting shelter is arranged to prevent said brushing bristles from directly contacting with an oral cavity of said user so as to prevent oral issues of said user from being damaged, wherein said spitting shelter comprises a sliding joint slidably coupled at said brush arm and a C-shaped bristle shelter upwardly extended from said sliding joint, wherein when said sliding joint is slid upwardly along said inserting end portion of said brush arm, said bristle shelter covers said brushing bristles which are not brushing on the tooth surface, wherein said sliding joint has a slider through hole having a size slightly larger than a size of said inserting end portion of said brush arm, wherein said inserting end portion of said brush arm is slidably passing through said slider through hole of said sliding joint to slidably mount said spitting shelter to said brush arm, wherein said driving shaft is extended through said inserting end portion of said brush arm to couple with said bristle end portion of said brush arm such that said bristle end portion of said brush arm is driven to rotate said brushing bristles about said driving shaft, wherein said driving shaft is coupled with said inserting end portion of said brush arm such that when said driving shaft is driven to rotate, said entire brush arm is rotated to roll said brushing bristles.

3. The electrical toothbrush, as recited in claim 2, wherein said power unit further comprises a rechargeable battery received in said receiving cavity of said handle body to electrically connect with said motor, wherein said handle body further has a recharging end electrically extended from said rechargeable battery for recharging said rechargeable battery when said recharging end of said handle body is electrically connected to a power source.

* * * * *